United States Patent [19]
DelGiorno et al.

[11] Patent Number: 4,732,038
[45] Date of Patent: Mar. 22, 1988

[54] MUSCLE TESTING METHOD

[76] Inventors: Daniel DelGiorno, 56 Meadow Glen Rd., Fort Salonga, N.Y. 11768; Mystical DelGiorno, 242 E. 72nd St. Apt. 1E, New York, N.Y. 10021

[21] Appl. No.: 884,718

[22] Filed: Jul. 11, 1986

[51] Int. Cl.$^4$ .............................................. A61B 5/22
[52] U.S. Cl. ...................................... 73/379; 128/782
[58] Field of Search ............... 73/379, 865.4; 128/774, 128/779, 781, 782

[56] References Cited

U.S. PATENT DOCUMENTS

| | | |
|---|---|---|
| 2,255,711 | 9/1941 | Noor . |
| 2,342,019 | 2/1944 | Solinski . |
| 2,590,055 | 3/1952 | Timmerman . |
| 2,644,334 | 7/1953 | Perry . |
| 2,680,967 | 6/1954 | Newman . |
| 2,860,514 | 11/1958 | Lauru . |
| 3,045,667 | 7/1962 | Sellner et al. . |
| 3,081,634 | 3/1963 | Blaszkowski . |
| 3,158,028 | 11/1964 | Chope . |
| 3,174,343 | 3/1965 | Kasulis . |
| 3,285,070 | 11/1966 | McDonough . |
| 3,297,021 | 1/1967 | Davis et al. . |
| 3,374,675 | 3/1968 | Keropian . |
| 3,375,717 | 4/1968 | Impellizzeri et al. . |
| 3,395,698 | 8/1968 | Morehouse . |
| 3,442,132 | 5/1969 | De Mare . |
| 3,465,592 | 9/1969 | Perrine . |
| 3,474,776 | 10/1969 | O'Brien . |
| 3,670,573 | 6/1972 | Kroemer . |
| 3,717,857 | 2/1973 | Evans . |
| 3,752,144 | 8/1973 | Weigle, Jr. . |
| 3,894,437 | 7/1975 | Hagy et al. . |
| 3,995,492 | 12/1976 | Clynes . |
| 4,114,449 | 9/1978 | Dikeman et al. . |
| 4,231,255 | 11/1980 | Haski et al. . |
| 4,236,528 | 12/1980 | Stanec et al. .................. 128/782 X |
| 4,307,608 | 12/1981 | Useldinger et al. . |
| 4,333,340 | 6/1982 | Elmeskog . |
| 4,375,674 | 3/1983 | Thornton .......................... 73/379 X |
| 4,462,252 | 7/1984 | Smidt et al. . |
| 4,501,148 | 2/1985 | Nicholas et al. . |
| 4,534,557 | 8/1985 | Bigelow et al. . |
| 4,592,371 | 6/1986 | Pellicano et al. ................. 73/379 X |
| 4,614,479 | 9/1986 | Liu . |

FOREIGN PATENT DOCUMENTS 2912981  10/1980  Fed. Rep. of Germany ...... 128/782

OTHER PUBLICATIONS

R. H. Nathan, "A Dynamometer for Biomechanical Use", J. Biomed. Eng., Apr. 1979, vol. 1, No. 2, pp. 83–88.

Primary Examiner—Charles A. Ruehl
Attorney, Agent, or Firm—Scully, Scott, Murphy & Presser

[57] ABSTRACT

A method of testing the strength of a selected muscle or muscle group, comprising the steps of stabilizing a subject's body, and determining the range of motion of a body area moved by the selected muscle or muscle group. A force sensing device is located in that range of motion, the sensing device is contacted with the above-mentioned body area, and the subject flexes the selected muscle or muscle group to force the body area against the sensing device. The selected muscle or muscle group is isolated so that at least substantially all the force applied to the sensing device is due to the flexing of the selected muscle or muscle group. The method further comprises the steps of measuring the force applied against the sensing device for a selected test period, and producing a signal representing the measured force.

64 Claims, 38 Drawing Figures

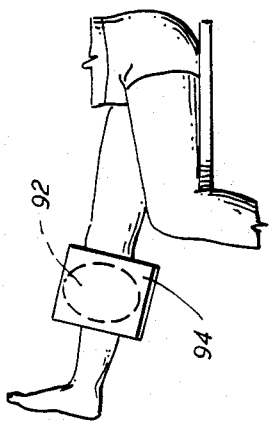
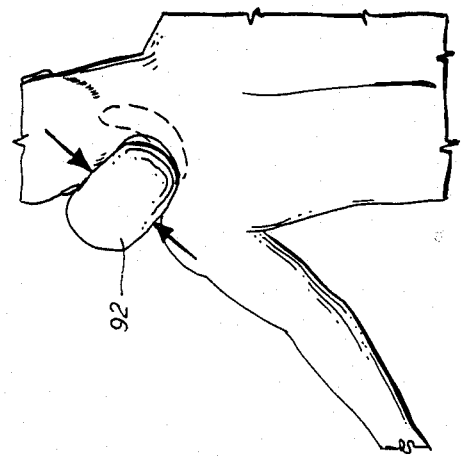
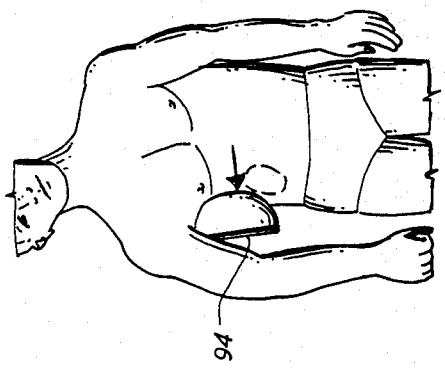
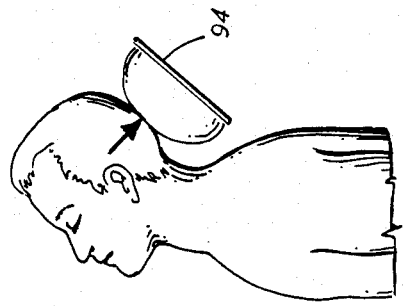
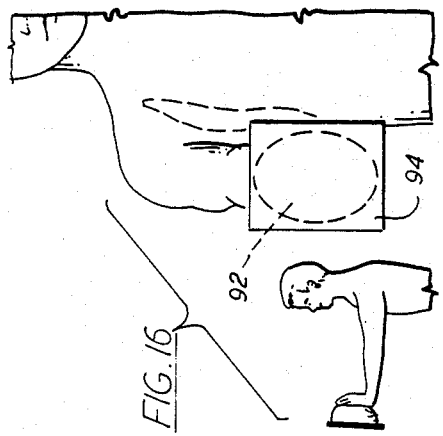
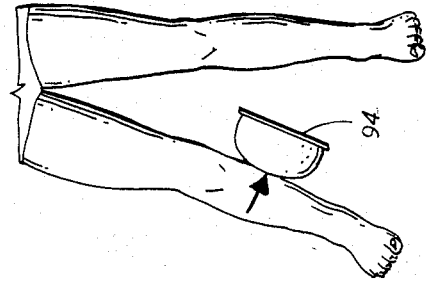

MUSCLE TESTING METHOD

BACKGROUND OF THE INVENTION

This invention generally relates to methods for testing the strengths and endurance of particular muscles and muscle groups, and more specifically, to methods of this type where a subject is positioned and applies a force to a sensing means in such a way that this force is due solely, or substantially solely, to a selected muscle or muscle group.

An accurate and objective measurement of the strengths of individual muscles is very helpful for several reasons. For example, as a therapeutic aid, such a measurement helps a therapist identify specific muscles that need to be strengthened and to design a program that will help those particular muscles. Moreover, a quantitative measurement will tell not only which muscles are weak, but also how weak those muscles are. Also, as a person is undergoing treatment, an objective measure of the progress he or she is making, first, helps the therapist modify the treatment program, if necessary, and second, allows the patient to witness personally the fact that his or her muscles are getting stronger with therapy, which often encourages the patient to continue the treatment. In addition, often a patient may believe he or she is fully recovered and will discontinue treatment; however, an accurate, quantitative and objective measure of the strength of the muscles may show otherwise, and convince the patient to continue treatment.

As an exercise or athletic training aid, an objective and quantitative measurement of the strength of individual muscles will help a person or a trainer develop a highly personalized exercise program that concentrates on the muscles that need the most work. Occasional retesting will enable an individual, first, to observe personally the progress he or she is making, and second, will help show how effective a particular exercise program is and, if it becomes advisable to do so, how a program should be modified. An individual may test and record the strengths of his or her muscles while healthy to provide a personal standard; and if that person is later injured, he or she, while recovering, can compare his or her muscle strengths against that recorded standard to determine whether the muscles have adequately recovered before resuming a particular activity, thus lessening the risk of a re-injury or of a new injury.

Because the muscles of the human body are structurally and functionally so interrelated, it is difficult to measure accurately the strengths of many of the individual muscles and muscle groups. For example, to test the strength of a bicep muscle, a person may grip a sensing device and flex the bicep to apply an upward force on that sensing device. However, at the same time, the subject may, consiously or subconsciously bend his or her back or flex his or her legs to increase the force applied to the sensing device. If this happens, the total force sensed by the sensing device includes the forces developed by the back or leg muscles, and thus is not a precise indication of the force developed by the bicep. Similar difficulties are encountered when trying to measure the strengths of many of the other muscles and muscle groups; and because of these difficulties, prior to the present invention, there are no specific procedures to measure accurately and quantitatively the individual strengths of many of the muscles and muscle groups.

SUMMARY OF THE INVENTION

An object of this invention is to provide methods to measure objectively and accurately the individual strengths of many of the muscles and muscle groups.

Another object of the present invention is to provide a plurality of positions for a subject to apply a force to a sensing means, where each position isolates the force from a different muscle or muscle group.

These and other objectives are attained with a method of testing the strength of a selected muscle or muscle group, comprising the steps of stabilizing a subject's body, and determining the range of motion of a body area moved by the selected muscle or muscle group. A force sensing means is located in that range of motion, the sensing means is contacted with the above-mentioned body area, and the subject flexes the selected muscle or muscle group to force the body area against the sensing means. The selected muscle or muscle group is isolated so that at least substantially all the force applied to the sensing means is due to the flexing of the selected muscle or muscle group. The method further comprises the steps of measuring the force applied against the sensing means for a selected test period, and producing a signal representing the measured force.

Specific procedures have been developed for testing the following muscles: the sternocleidomastoid muscle, the anterior deltoid muscles, the pectoralis major muscles, the rectus abdominus muscle, the bicep muscles of the arms, the finger flexor muscles, the sartorius and gracilis muscles, the quadricep muscles, the anterior tibial muscles, the peroneus longus and peroneus brevis muscles, the subscapularis muscles, the coracobrachialis muscles, the serratus anterior muscles, the quadratus lumborum muscles, the psoas and iliacus muscles, the adductor longus and adductor magnus muscles, the neck extensor muscles and the upper trapezius muscles, the major and minor rhomboid and trapezius muscles, the deltoid muscles, the latissiumus dorsi and teres major muscles, the tricep muscles of the arm, the gluteus medius muscles, the gluteus maximus muscles, the biceps femorus, semitendinosus and semimembranosus muscles, the gastrocnemius muscles, the supraspinatus muscles, the teres minor muscles, the sacrospinalis muscles, and the piriformis muscles.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIGS. 16 through 21 show the positions of the sensing means and the subject to test, respectively, the serratus anterior muscles, the quadratus lumborum muscles, the psoas and iliacus muscles, the adductor longus and adductor magnus muscles, the neck extensor muscles, and the upper trapezius muscles.

DETAILED DESCRIPTION OF THE PREFERRED EMBODIMENTS

Figure 1:
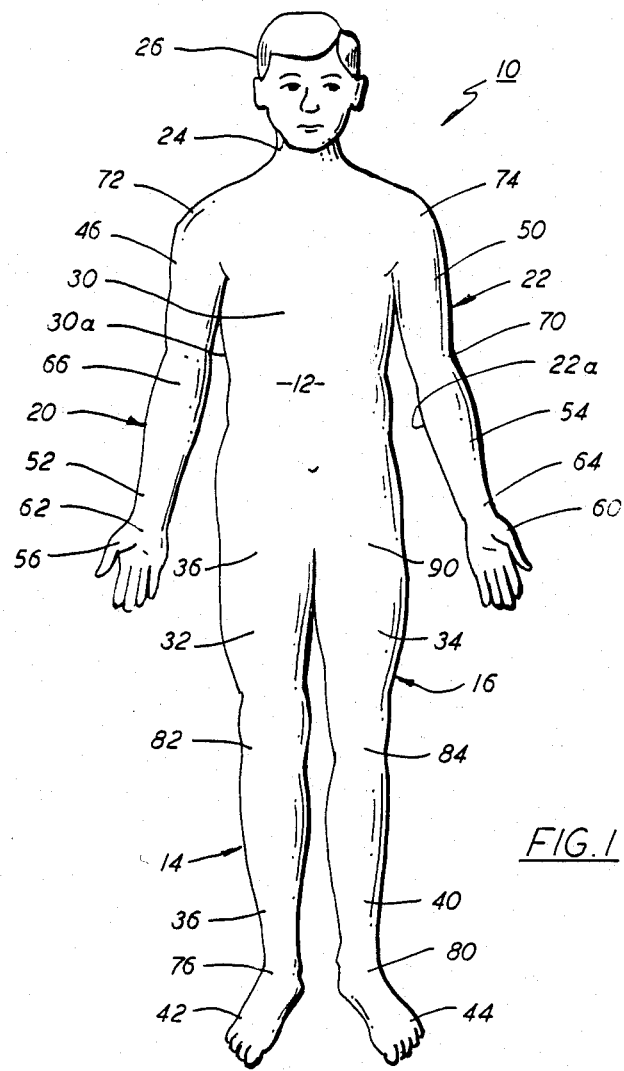
FIG. 1 is an outline of the human body.

FIG. 1 illustrates the body of a subject 10 comprising trunk 12, legs 14 and 16, arms 20 and 22, neck 24, and head 26. Trunk 12 includes chest 30; each leg 14, 16 includes thigh 32, 34, lower leg part 36, 40, and foot 42, 44; and each arm 20, 22 includes upper arm part 46, 50, forearm 52, 54, and hands 56, 60. Hands 56, 60 are connected to forearms 52, 54 by wrists 62, 64, the forearms are connected to upper arm parts 46, 50 by elbows 66, 70; and the upper arm parts are connected to trunk 12 by shoulders 72, 74. Feet 42, 44 are connected to lower leg parts 36, 40 by ankles 76, 80; the lower leg parts are connected to thighs 32, 34 by knees 82, 84; and the thighs are connected to trunk 12 by hips 86, 90.

As the terms are used herein, the forward direction refers to the direction subject 10 is facing, while the rearward direction is the opposite direction, and the lateral directions are the directions extending to the left and to the right sides of the subject as viewed in FIG. 1. Further, the outsides of the above-listed parts of the body of subject 10 are the exterior surfaces on the body parts that normally face away from the subject, either forwardly, rearwardly or laterally; and the insides of the above-listed body parts are the exterior surfaces on the body parts that normally face toward a vertical plane bisecting the body from front to back. For instance, 30a in FIG. 1 identifies an outside surface of the chest of the subject, and 22a in FIG. 1 identifies an inside surface of the left arm of the subject.

A complete apparatus that may be used to practice the present invention is described in detail below and in U.S. patent application Ser. No. 869,135, filed May 30, 1986, by Daniel DelGiorno, Russel A. Pellicano and Henry Medina, for "Muscle Testing Apparatus," the disclosure of which is herein incorporated by reference.

Figures 2, 3:
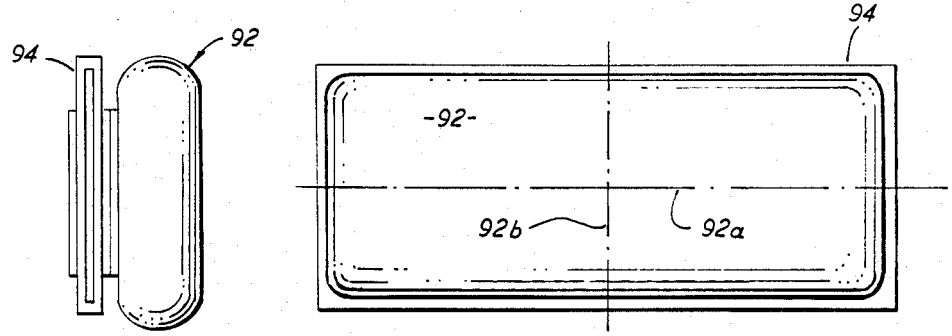
FIGS. 2 and 3 are side and front views, respectively, of a force sensing means that may be used in the practice of the present invention.

FIGS. 2 and 3 show a part of this apparatus, and in particular, a force sensing means 92. Generally, sensing means 92 comprises an inflatable bag or pressure pad releasably held on a rigid that support plate 94. Pad 92 has a generally rectangular shape, the longer axis 92a of the pad is referred to as its major axis, and the shorter axis 96b of the pad is referred to as the minor axis. The surface of pad 92 that is in direct contact with support plate 94 is referred to as the back of the pad, the opposite surface of the pad is referred to as the front of the pad, and the pad is considered as facing the direction that its front is facing.

In accordance with the present invention, numerous procedures are provided for testing the strengths of a multitude of individual muscles and muscle groups. Broadly, to test a particular muscle or muscle group, the procedure is to stabilize the body and isolate the muscle, test the range of motion of the muscle, bisect the arc created by that action, position the body as described below, and apply force by contracting the muscle against the testing surface. More specifically, to test a selected muscle or muscle group, the subject is stabilized—that is, located in a stable, balanced position—and the range or arc of movement of a body area moved by the selected muscle or muscle group is determined. Then, force sensing means 92 is located in that range of motion, and the force sensing means is contacted by the above-mentioned body area. The selected muscle or muscle group is flexed to force the body area against sensing means 92, the force applied against the sensing means is measured, and a signal is produced representing that measured force.

Preferably, sensing means 92 is located in a position bisecting the above-mentioned arc of movement of the body area, with the front face of the sensing means extending substantially perpendicular to the direction of the force applied to the sensing means by the body area. The arc of movement of a particular body area may vary from person to person, depending on the physical condition of the person. Also, the arc of movement of a selected body area of an individual may vary over time as the physical condition of the individual changes. For example, the range of movement of an arm of a person may be severely limited after an injury to the arm, and this range may improve dramatically with the appropriate therapy.

Figure 4:
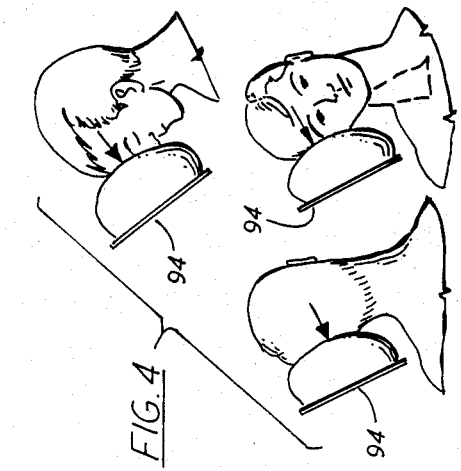

FIG. 4 illustrates the position of the pressure pad and the subject to test the sternocleidomastoid muscle, which causes the head to pivot forward and to the left and right sides. To test the strength with which the sternocleidomastoid causes the head to pivot to the left, the pressure pad is located to the left side of the subject's head, with the pressure pad facing toward the subject and with support plate 94 at about a 25°–30° angle with the vertical. The pressure pad is contacted with the side of the head, at about the level of, and slightly rearward of, the ear, and then the sternocleidomastoid muscle is flexed to apply an outward and downward force on the pressure pad. To test the strength with which the sternocleidomastoid muscle causes the head to pivot to the right, the pressure pad is located to the right side of the subject's head, again with the pressure pad facing toward the subject and with the support plate at about a 25° angle with the vertical. The pressure pad is contacted with the side of the head, at about the level of, and slightly forward of, the ear, and then the sternocleidomastoid muscle is flexed to apply a downward and outward force on the pressure pad.

To test the strength of the sternocleidomastoid to pivot the head forward, the pressure pad is located directly forward of the subject's face, facing toward the subject and with support plate 94 at an angle of about 35° to 40° to the vertical. The pad is contacted with the front of the head, for example the bridge of the nose and the central, front part of the forehead, and then the sternocleidomastoid is flexed to apply a downward and forward force on the pressure pad. With each of the above procedures for testing the sternocleidomastoid, the subject may be seated or standing during the procedure, although preferably the subject is seated in a chair with his or her legs and feet held relaxed, spaced above the floor or ground. It is also desireable to hold the subject firmly in the chair by a belt or strap anchored or connected to the chair and extending across the front of the subject's waist or hips.

Figure 5:
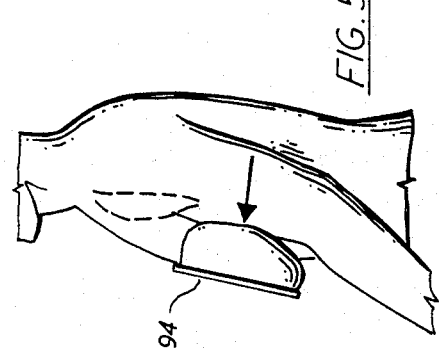

FIG. 5 illustrates the positions of the pressure pad and the subject to test an anterior deltoid muscle. To test the left anterior deltoid, the pressure pad is located directly forward of and facing the left arm of the subject, the pad is contacted with the front of that arm, and then the left anterior deltoid is flexed to apply a forward and upward force to the pressure pad. Preferably, the pressure pad is located at a height between the subject's left shoulder and elbow, with the support plate 94 slanting downwardly forwardly at an angle of about 10° to 15° to the vertical, and the pad is contacted with the front of the upper part of the left arm. An analogous procedure may be used to test the right anterior deltoid.

Figure 6:
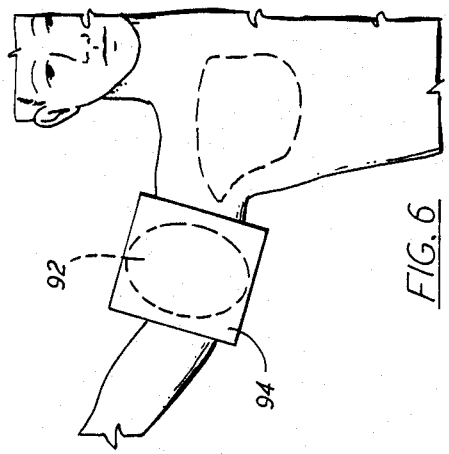
FIGS. 4 through 9 show different positions of a subject and the force sensing means for testing, respectively, the sternocleidomastoid muscle, the anterior deltoid muscles, the pectoralis major muscle, the rectus abdominus muscle, the bicep muscles of the arms, and the finger flexor.

FIG. 6 shows the positions of the pressure pad and the subject to test a pectoralus major muscle. To test the right pectoralus major muscle, the pressure pad is located forward of and to the right side of the subject, at a height about level with the subject's right shoulder. The right arm is extended to the side and slightly upward from the right shoulder, and the pressure pad is contacted with the front of the right arm, preferably with the front of the upper part of the right arm. Then, the right pectoralus major muscle is flexed to apply a forward force on the pressure pad. An analogous procedure may be used to test the strength of the left pectoralus major muscle.

With the procedures illustrated in FIGS. 5 and 6, the subject may be seated or standing, although preferably the subject is seated in a chair with his or her legs and feet held relaxed, spaced above the ground or floor. It is also desireable to hold the subject firmly in the chair by a belt or strap anchored or connected to the chair and extending across the front of the subject's waist or hips.

Figure 7:
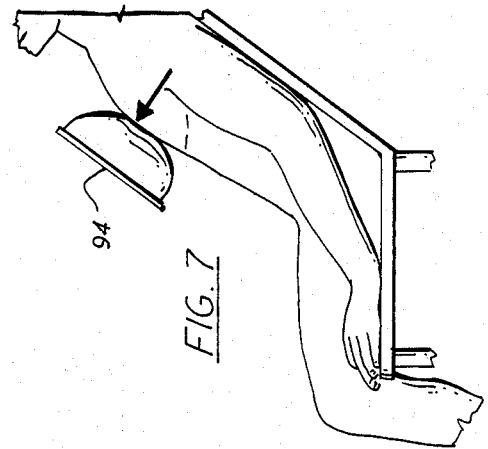

FIG. 7 illustrates the position of the pressure pad and the subject to test the rectus abdominus muscle, generally referred to as the abdominal muscles. For this test, the patient is seated in a chair with his or her back reclining against the back of the chair, at an angle of about 35° to the vertical. The pressure pad is located directly in front of the top part of the subject's chest, facing toward the chest, and with the support plate 94 also at an angle of about 35° to the vertical. The pressure pad is contacted with an upper, central area on the front of the chest, and the abdominal muscles are flexed to apply an upward and outward force on the pressure pad. The subject's thighs may be held on the chair to prevent the subject from raising and then lowering the thighs to develop an additional force on the pressure pad. Preferably, the subject is firmly held in the chair by a belt or strap connected or anchored to the chair and extending across the front of the subject's waist or hips, and the subject is seated in the chair with his or her legs and feet held relaxed, spaced above the ground or floor.

Figure 8:
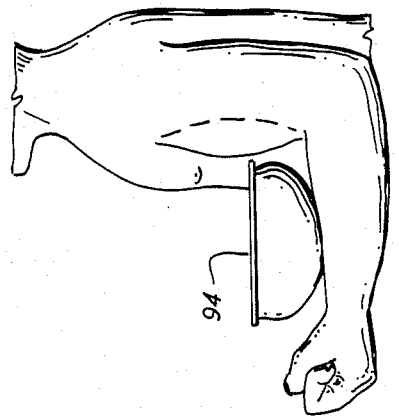

FIG. 8 shows the positions of the pressure pad and the subject to test the bicep muscle of the left arm. The pressure pad is located directly forward of the left arm of the subject, with the support plate 94 substantially horizontal, and with the pressure pad facing downward and extending slightly below the top of the subject's left elbow. The subject pivots the left forearm upward, contacts the pressure pad with the top of the left forearm, and flexes the bicep of the left arm to apply an upward force to the pressure pad. Preferably, for this test, the left forearm is pivoted upward to a generally horizontal position, the subject contacts the pressure pad with the left forearm about midway along its length between the left wrist and elbow, and the upper part of the left arm is held generally vertical. An analogous procedure may be used to test the bicep of the right arm.

Figure 9:
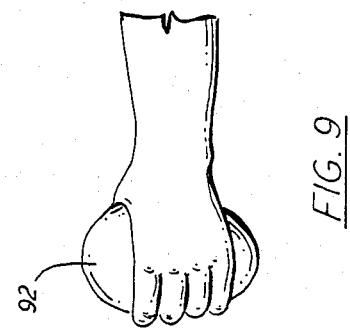

FIG. 9 shows the positions of the pressure pad and the subject to test the finger flexor muscles, which are those muscles used to flex the thumb and fingers. The finger flexor muscles include the flexor carpi radialis, the flexor carpi ulnaris, and the flexor digitorum superifcialis. For this procedure, the pressure pad is taken off of support plate 94, and is held and squeezed between the thumb and fingers of one of the subject's hands. In particular, the first four fingers of the hand are held against one side of the pressure pad, the thumb is held against an opposite side of the pad, and the finger flexor muscles are contracted to squeeze the pressure pad between the fingers and the thumb. FIG. 9 specifically shows a procedure for testing the finger flexor muscles of the left hand, and an analogous procedure may be used to test the finger flexor muscles of the right hand.

With the procedures illustrated in FIGS. 8 and 9, the subject may be seated or standing, although preferably the subject is seated in a chair with his or her legs and feet held relaxed, spaced above the ground or floor. It is also preferred to hold the subject firmly in the chair by a belt or strap anchored or connected to the chair and extending across the front of the subject's waist or hips.

Figure 10:
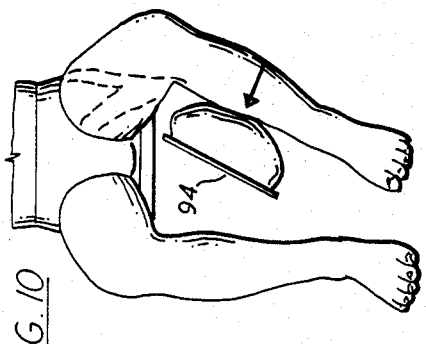

The positions of the pressure pad and the subject to test the left sartorius and gracilus muscles are shown in FIG. 10. The pressure pad is located between the legs of the subject, facing the left leg, with support plate 94 at an angle of about 25° to the vertical. The subject engages the pressure pad with the inside of the lower part of the left leg, about midway between the left ankle and the knee, and flexes the left sartorius and gracilus muscles to apply an upward and inward force on the pressure pad. As would be appreciated, an analogous method may be used to test the right sartorius and gracilus muscles.

Figure 11:
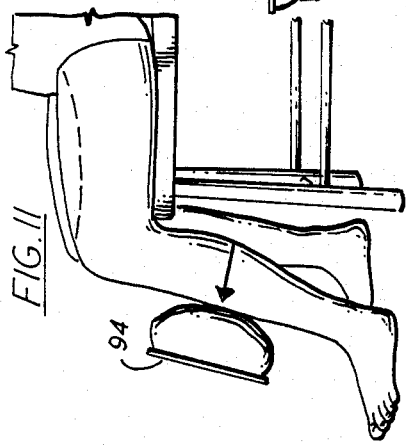

FIG. 11 shows the positions of the pressure pad and the subject to test the left quadriceps. The pressure pad is located directly in front of the lower part of the left leg, facing toward that leg, and with the support plate 94 at an angle of about 12° to 15° to the vertical. The subject engages the pressure pad with the front of the lower part of the leg, about midway between the left knee and ankle, and flexes the left quadriceps to apply a forward and upward force on the pressure pad.

Figure 12:
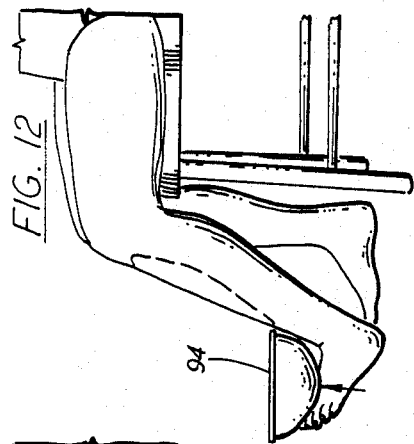
FIGS. 10 through 15 show the positions of the sensing means and the subject to test, respectively, the sartorius and the gracilius muscles, the quadricep muscles, the anterior tibial muscles, the peroneus longus and the peroneus brevis muscles, the subscapularis muscles, and the coracobrachialis muscles.

FIG. 12 shows the positions of the pressure pad and the subject to test the left anterior tibial muscle. The pressure pad is located directly forward of the left leg, facing downward and with the support plate 94 at an angle of about 25° to 30° to the horizontal. The subject pivots the lower part of the left leg forward slightly, contacts the pressure pad with the top of the left foot, and flexes the anterior tibial muscle to apply an upward and rearward force on the pressure pad. Preferably, care is taken to prevent the subject from flexing the thigh muscles or from raising the thighs to develop additional forces on the pressure pad.

FIGS. 10, 11 and 12 show procedures for testing muscles on the left side of the body; and, as will be understood, analogous procedures may be used to test the right sartorius and gracilus muscles, the right quadriceps, and the right anterior tibial muscle.

Figure 13:
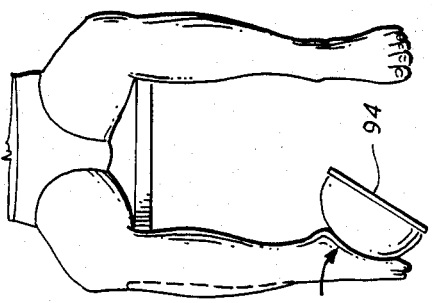

FIG. 13 shows the positions of the pressure pad and the subject to test the right peroneus longus and peroneus brevis muscles. The pressure pad is located between the legs of the subject at about the level of and adjacent the subject's right foot, with the pressure pad facing outward toward the right leg and with the support plate 94 at an angle of about 30° to the vertical. The subject engages the pressure pad with the bottom of the right foot, preferably with the left side of the bottom of that foot, and flexes his or her right peroneous longus and peroneous brevice muscles to apply a downward and laterally inward force on the pressure pad. Of course, an analogous procedure may be used to test the left peroneus longus and peroneus brevis muscles.

With the procedures illustrated in FIGS. 10-13, it is preferred to have the subject seated in a chair with his or her legs and feet held relaxed, above the ground or floor, and it is desireable to hold the subject firmly in the chair by a seat belt or strap anchored or connected to the chair and extending across the front of the subject's waist or hips.

Figure 14:
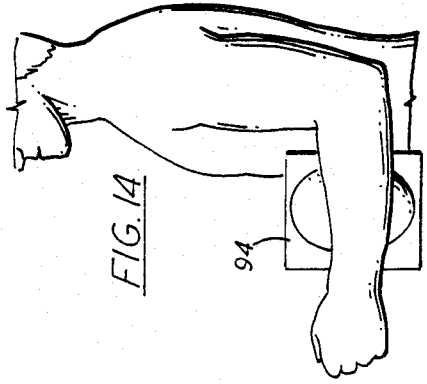

FIG. 14 illustrates the positions of the pressure pad and the subject to test the left subscapularis muscle. The pressure pad is located forward of and laterally slightly inward of the left arm, at about the height of the left elbow, with the support plate 94 substantially vertical and the pressure pad facing laterally directly outward. The subject raises the left forearm to a substantially horizontal position, engages the pressure pad with an inside of the left forearm, and flexes the left subscapularis muscle to apply an inward force to the pressure pad. It is advantageous to keep the upper part of the left arm vertical during the procedure; and of course, an analogous method may be employed to test the right subscapularous muscle.

Figure 15:
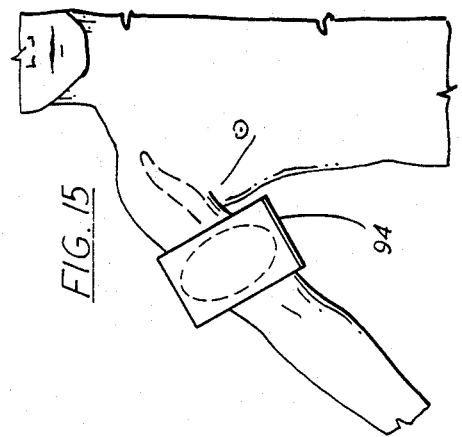

The positions of the pressure pad and the subject to test the right coracobrachialis muscle are shown in FIG. 15; and the pressure pad is located forward of the subject and laterally outward of the right arm, with the pad facing laterally outward and slightly downward and rearward. The subject extends the right arm forwardly, downwardly and also slightly laterally outwardly, engages the pressure pad with an inside of the arm, and flexes the right coracobrachialis muscle to apply an upward and inward force to the pressure pad. Preferably, the pressure pad is located at a level slightly below the the right shoulder, and the subject engages the pad with an inside of the upper part of the right arm, slightly above the elbow, and it is also desirable to have the subject keep the right forearm and the upper part of the right arm aligned, or straight, during this procedure. An analogous procedure may be used to test the left coracobrachialis muscle.

For the test shown in FIGS. 14 and 15, the subject may be seated or standing, although preferably the subject is seated in a chair with his or her legs and feet held relaxed, above the ground or floor. It is also preferred to hold the subject securely in the chair by a belt or strap anchored or connected to the chair and extending across the front of the subject's waist or hips.

FIG. 16 shows the procedure for testing the serratus anterior muscles. To test the right serratus anterior muscles, the pressure pad is located forward of the subject, facing rearward toward the subject. The subject raises the right arm, places the right hand against the pressure pad, and flexes the right serratus anterior muscles to apply a forward force on the pressure pad. Preferably, the pressure pad is located directly forward of the right shoulder, and the subject raises the right arm to a substantially horizontal position to engage the pressure pad. In addition, with a preferred embodiment, the subject contacts the pressure pad by placing the palm of the right hand against the pad, and the subject keeps the upper part of the right arm and the right forearm aligned, or straight, as the force is applied to the pressure pad. The subject may be either sitting or standing, although preferably the subject is standing, and it is also desirable to keep the subject standing or sitting up straight so that he or she does not lean into the pressure pad. Of course, an analogous procedure may be used to test the left serratus anterior muscle.

FIG. 17 illustrates the position of the pressure pad and the subject to test the right quadratus lumborum muscle. The pressure pad is located between the chest and the right arm of the subject, facing inward toward the chest, with the support plate 94 at an angle of about 8° to 10° to the vertical. The subject engages the pressure pad with the right side of the chest, and flexes the right quadratus lumborum muscle to apply an outward force on the pressure pad. The subject may be either sitting or standing, however, preferably he or she is seated in a chair with his or her legs and feet held relaxed, spaced above the ground or floor. It is also desireable to hold the subject firmly in the chair by a belt or strap anchored or connected to the chair and extending across the front of the subject's waist or hips. An analogous method may be used to test the left quadratus lumborum.

FIG. 18 shows the position of the pressure pad and the subject to test the right psoas and iliacus muscles. The patient is seated, and the pressure pad is located laterally between and slightly above the legs of the subject, with the pressure pad facing slightly downward and laterally outward toward the right of the subject. The subject raises the right leg, engages the pressure pad with the inside of the leg, and flexes the right psoas and iliacus muscles to apply a laterally inward and upward force on the pressure pad. Preferably, the pressure pad is located slightly forward of the subject's legs when the subject is in the seated position, the subject contacts the pressure pad by raising both the right thigh and the lower part of the right leg, and engages the pressure pad with the inside of the lower part of the right leg. Preferably, the subject is firmly held in the chair by a belt or strap connected or anchored to the chair and extending across the front of the subject's waist or hips, and the subject is seated in the chair with his or her left leg and foot held relaxed, spaced above the ground or floor. It is desirable to keep the right thigh and the lower part of the right leg aligned, or straight, during this procedure; and, of course, an analogous procedure may be used to test the left psoas and iliacus muscles.

FIG. 19 illustrates the positions of the pressure pad and the subject to test the right adductor longus and adductor magnus muscles. The pressure pad is located between the legs of the subject, facing laterally outward toward the right leg, with the support plate 94 at an angle of about 25° to the vertical. The subject engages the pressure pad with the inside of the right leg, and flexes the right adductor longus and adductor magnus muscles to apply a downward and inward force on the pressure pad. Preferably, the pressure pad is located between the lower parts of the legs of the subject, and the subject engages the pressure pad with the inside of the calf of the right leg. Also, it is desirable to have the subject standing for this procedure and to keep the thigh and the lower part of the right leg straight. As will be understood, an analogous procedure may be used to test the left adductor longus and adductor magnus muscles.

FIG. 20 shows the procedure to test neck extensor muscles, and specifically the splenius capitis and cervicis muscle. The pressure pad is located directly behind the back of the neck and the back of the lower head, with the pressure pad facing upwards and towards the subject, and with the support plate 94 at an angle of about 40° to 45° to the vertical. The subject bends his or her head backwards to engage the pressure pad with the center of the back of the head, and flexes the splenius capitis and cervicis muscle to apply a rearward and downward force on the pressure pad.

FIG. 21 illustrates the positions of the pressure pad and the subject to test the left upper trapezius muscle. The pressure pad is removed from the support plate, held between the left shoulder and the left side of the head, behind the ear of the subject, and then squeezed between the shoulder and the head. Preferably, the left shoulder is raised slightly and the left arm is pivoted laterally outward to an angle of about 45° with the horizontal to help hold the pressure pad on the shoulder. As will be understood, an analogous process may be used to test the right upper trapezius muscle.

For the methods shown in FIGS. 20 and 21, the subject may be seated or standing, although preferably the subject is seated in a chair with his or her legs and feet held relaxed, above the ground or floor. It is also desireable to hold the subject securely in the chair by a belt or strap anchored or connected to the chair and extending across the front of the subject's waist or hips.

Figure 22:
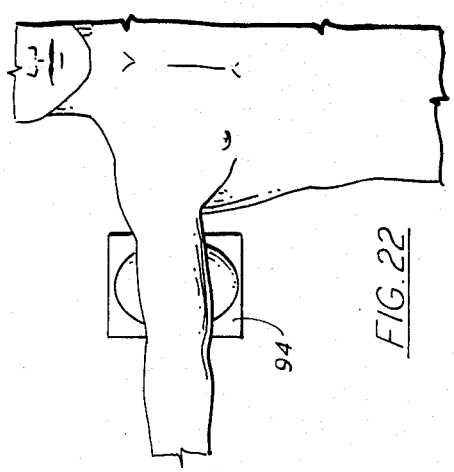

FIG. 22 shows the positions of the pressure pad and the subject to test the right major and minor rhomboid and the right trapezeius muscles. The pressure pad is located to the right side of the subject, facing directly forward. The subject pivots the right arm laterally outward and upward, engages the pressure pad with the back of the right arm, and flexes the right major and minor rhomboid and the right trapezeius muscles to apply a rearward force on the pressure pad. Preferably, the pressure pad is located at the level of the right shoulder, slightly rearward of and slightly to the right side of the subject; and the subject pivots the right arm upward to a substantially horizontal position and engages the pressure pad with the back of the upper part of the right upper arm, about midway between the right shoulder and elbow. It is desirable to keep the upper part of the right arm and the right forearm aligned, or straight, or during the testing process.

Figure 23:
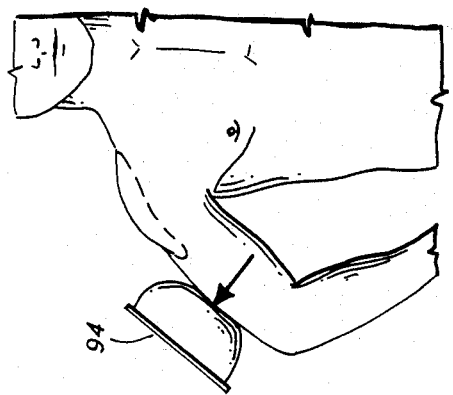

FIG. 23 shows the positions of the subject and the pressure pad to test the right deltoid muscle. For this method, the pressure pad is located laterally to the right side of the subject, at a level slightly below the top of the right shoulder, The pressure plate faces downward and laterally inwardly, and the support plate 94 is at an angle of about 50° to the vertical. The subject pivots the right arm laterally outward, engages the pressure pad with the outside of the arm, and flexes the right deltoid to apply an upward and outward force on the pressure pad. Preferably, the pressure pad is engaged with the outside of the upper part of the right arm, about midway between the shoulder and the elbow, and the right arm is bent at the elbow so that the forearm is held at about 90° relative to the upper part of the right arm. Further, care should be taken so that the subject does not apply an upward force on the pressure pad by flexing any leg or back muscles.

Figure 24:
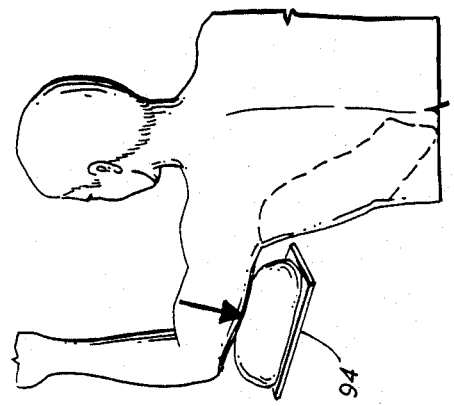
FIGS. 22 through 27 show the positions of the sensing means and the subject, respectively, to test the major and minor rhomboid and the trapezius muscles, the deltoid muscles, the latissiumus dorsi and the teres major muscles, the tricep muscles, the gluteus medius muscles, and the gluteus maximus muscles.

The method to test the left latissimus dorsi and teres major muscles is illustrated in FIG. 24. The pressure pad is located to the left and forward of the subject, at a level slightly below the top of the left shoulder. The pressure pad faces upward, and the support plate 94 is substantially horizontal and slanting rearwardly toward the right as viewed in FIG. 24. The subject raises the left arm and extends it forwardly and laterally outwardly so that it extends directly above the pressure pad. The subject engages the pressure pad with the bottom of the left arm, and flexes the left latissimus dorsi and teres major muscles to apply a downward and inward force on the pressure pad. Preferably, the left forearm is held in a vertical position, and the pressure pad is engaged by the bottom of the upper part of the left arm.

Figure 25:
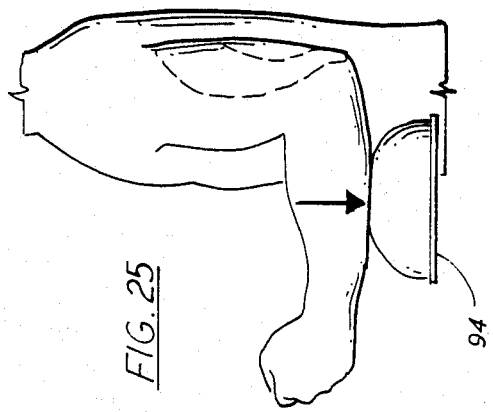

FIG. 25 shows the process for testing the left triceps. With this process, the pressure pad is located directly forward of the left arm, facing upwards. The top of the pressure pad is about the level of the left elbow, and the support plate 94 is substantially horizontal. The subject moves the left forearm to a horizontal position, engages the pressure pad with the bottom of the forearm, and contracts the left triceps to apply a downward force on the pressure pad. Preferably, the upper part of the left arm is held in a vertical position, and the left forearm is held with the palm of the left hand directed laterally inward.

With the processes depicted in FIGS. 22-25, the subject may be seated or standing, although it is preferred to have the subject seated in a chair with his or her legs and feet held relaxed, spaced above the ground or floor. It is also desireable to hold the subject firmly in the chair by a belt or strap anchored or connected to the chair and extending across the front of the subject's waist or hips.

Figure 26:
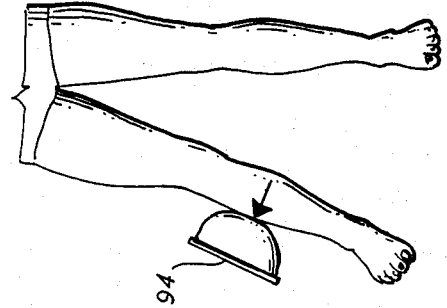

FIG. 26 shows the positions of the pressure pad and the subject to test the right gluteous medius muscle; and in particular, the pressure pad is located laterally outside the right leg, facing inward and downward and with the support plate 94 at an angle of about 25° to the vertical. The pressure pad is engaged by the outside of the right leg, and the subject flexes the right gluteous medius muscle to apply an outward and upward force on the pressure pad. Preferably, the pressure pad is positioned so that it engages the outside of the calf of the right leg, and the right thigh and the lower part of the right leg are aligned, or straight, as the right leg is flexed against the pressure pad. It is preferred to conduct this procedure with the subject standing, and it is desirable to take care that the subject does not lean into the pressure pad or apply any forces thereon by flexing muscles of the left leg.

Figure 27:
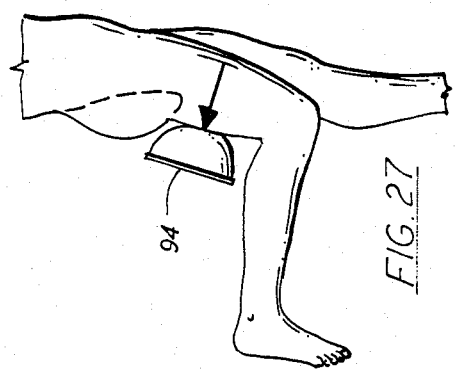

A procedure for testing the right gluteous maximus muscle is shown in FIG. 27. The pressure pad is located directly behind the right leg, with the pressure pad facing forward and with the support plate 94 at an angle of about 20° to the vertical. The subject engages the pressure pad with the back of the right leg, and then flexes the right gluteous maximus muscle to apply a rearward and upward force on the pad. Preferably, the pressure pad is located at a level slightly below the right hip, and the pad is engaged by the back of the right thigh. In addition, preferably, while the force is applied to the pressure pad, the right leg is bent at the knee and the lower part of the right leg is held in an approximately horizontal position. It is desirable to conduct this test when the patient is standing; and, here too, care should be taken to prevent the subject from leaning into the pressure pad.

FIGS. 22, 23, 26 and 27 show procedures for testing muscles on the right side of the subject, and analogous methods may be used to test the corresponding muscles on the left side of the subject. Likewise, FIGS. 24 and 25 depict procedures for testing muscles on the left side of the subject, and analogous methods may be used to test corresponding muscles on the subject's right side.

Figure 28:
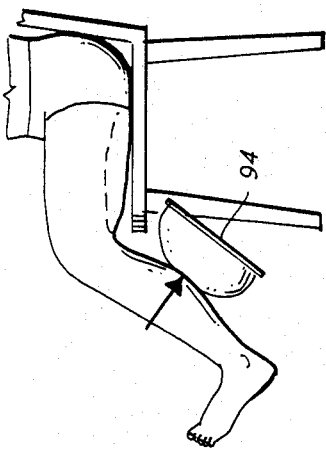
FIGS. 28 through 33 show the positions of the sensing means and the subject, respectively, to test the bicep femorus, semitendinosus and the semimembranosus muscles, the gastrocnemius muscles, the supraspinatus muscles, the teres minor muscles, the sacrospinalis muscles, and the piriformis muscles.

FIG. 28 shows the positions of the pressure pad and the subject to test the left biceps femoris, semitendinosus and semimembranosus muscles, generally referred to as the hamstring muscles. For this procedure, the subject is seated, with the lower part of the left leg extending forwardly downwardly, and the pressure pad is located directly rearward of the left leg, with the pressure pad facing forward and upward and with the support plate 94 at an angle of about 40° to the vertical. The subject engages the pressure pad with the back of the left leg, preferably the back of the left calf, and flexes the left semitendinosus and semimembranosus muscles to apply a downward and rearward force on the pressure pad. With this method, preferably the subject is firmly held in the chair by a belt or strap connected or anchored to the chair and extending across the front of the subject's waist or hips, and the subject is seated in the chair with both legs and both feet held above the ground or floor, and with the right leg and foot held relaxed.

Figure 29:
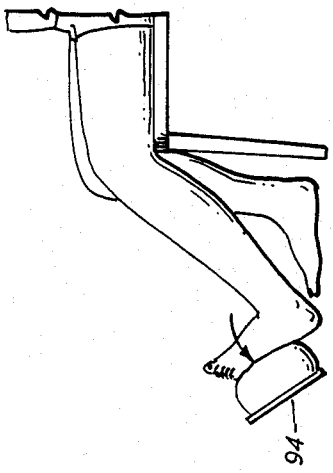

FIG. 29 illustrates the positions of the pressure pad and the subject to the test the left gastrocnemius muscle. The subject is seated, and the pressure pad is located directly forward of the left leg, with the pressure pad facing upward and rearward and with the support plate 94 at an angle of about 32° to the vertical. The subject places the bottom of the left foot, preferably near the ball of that foot, on the pressure pad, and flexes the left gastracnemius muscle to apply a downward and forward force on the pressure pad. With this method, also, it is preferred to hold the subject firmly in the chair by a belt or strap connected or anchored to the chair and extending across the front of the subject's waist or hips, and the subject is seated in the chair with both legs and both feet held above the floor or ground and with the right foot and leg held relaxed.

Figure 30:
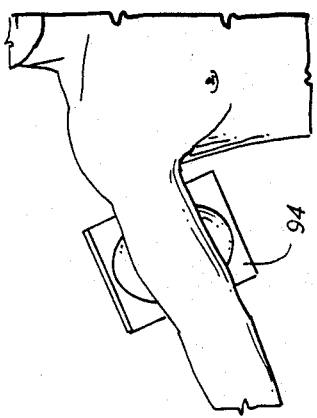

The positions of the pressure pad and the subject to test the right supraspinatus muscle are shown in FIG. 30. For this procedure, the pressure pad is located slightly behind and to the right of the subject, with the pad facing forward and downward slightly. The subject pivots the right arm laterally outward to an angle of about 60° to the vertical, engages the pressure pad with the back of the arm, and flexes the right supraspinatus to apply an upward and rearward force to the pressure pad. Preferably, the pressure pad is centered just to the side of and slightly below the level of the right shoulder, with the minor axis of the pressure pad parallel to the axis of the upper part of the arm, and the subject engages the pressure pad with the back of the upper part of the right arm. It is also desirable to have the subject keep the right forearm and the upper part of the right arm straight and to keep the palm of the right hand directed forwardly during this procedure.

Figure 31:
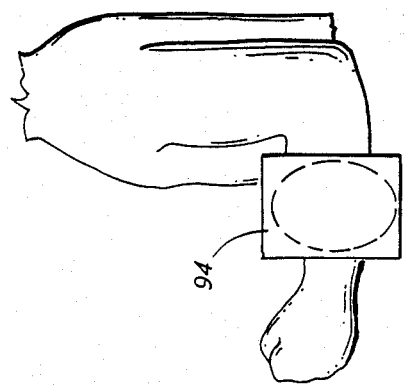

FIG. 31 shows the positions of the pressure pad and the subject to test the left teres minor muscle. The pressure pad is positioned forward and laterally slightly outward of the left arm, with the center of the pad located at about the level of the left elbow. The subject raises the left forearm to a substantially horizontal position, engages the pressure pad with the outside of the forearm, and flexes the left teres minor muscle to apply an outward force to the pressure pad. In either case, it is advantageous to keep the upper part of the left arm vertical during this test, and to position the forearm so that the left palm is directed inward.

With the processes depicted in FIGS. 30 and 31, the subject may be seated or standing, although it is preferred to have the subject seated in a chair with his or her legs and feet held relaxed, spaced above the ground or floor. It is also desireable to hold the subject firmly in the chair by a belt or strap anchored or connected to the chair and extending across the front of the subject's waist or hips.

Figure 32:
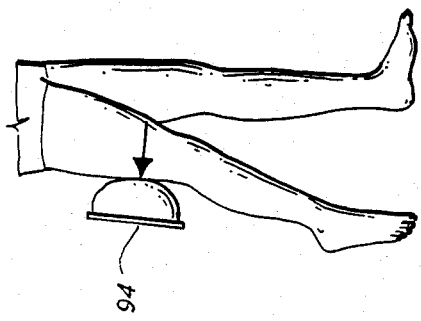

FIG. 32 shows the method for testing the right sacrospinalis muscle. The pressure pad is located directly behind the right leg, with the pressure pad facing forward and the support plate 94 at an angle of about 5° or 6° to the vertical. The subject engages the pressure pad with the back of the right leg, and then flexes the right sacrospinalis muscle to apply a rearward and slightly upward force on the pressure pad. Preferably, the pressure pad is located at a level slightly above the top of the right knee, and the pad is engaged by the back of the right thigh. In addition, preferably, while the force is applied to the pressure pad, the lower part of the right leg is held straight with the right thigh, and the right foot is flexed downward about the right ankle so that the foot points substantially downward. It is desirable to conduct this test when the patient is standing and it is also desirable to take care to be sure, first, that the subject does not lean into the pressure pad, and second, that the right foot is kept off the floor so that the patient does not push that foot against the floor to increase the force applied to the pressure pad.

Figure 33:
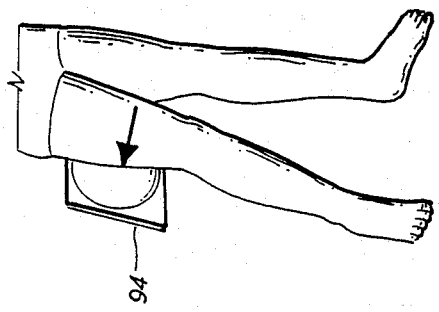

FIG. 33 shows the positions of rhe pressure pad and the subject to test the right piriformis muscle. The pressure pad is located slightly rearward of and to the right side of the right leg, with the pressure pad facing forwardly, and slightly downwardly and laterally inwardly. The subject engages the pressure pad with the right side of the back of the right leg and flexes the right piriformis to apply a rearward and outward force on the pad. Preferably, the the pressure pad is at a level about midway between the right hip and the right knee, and the pressure pad is contacted with the back of the right thigh. It is desirable to conduct this procedure when the patient is standing, to hold the lower part of the right leg aligned with the right thigh, and to keep the right foot off the floor.

FIGS. 28, 29 and 31 show methods for testing muscles on the left side of the subject's body; and, as will be understood by those skilled in the art, analogous procedures may be used to test corresponding muscles on the right side of the body. Similarly, FIGS. 30, 32 and 33 illustrate procedures for testing muscles on the right side of the body, and analogous procedures may be used to test corresponding muscles on the subject's left side.

Figures 34, 35:
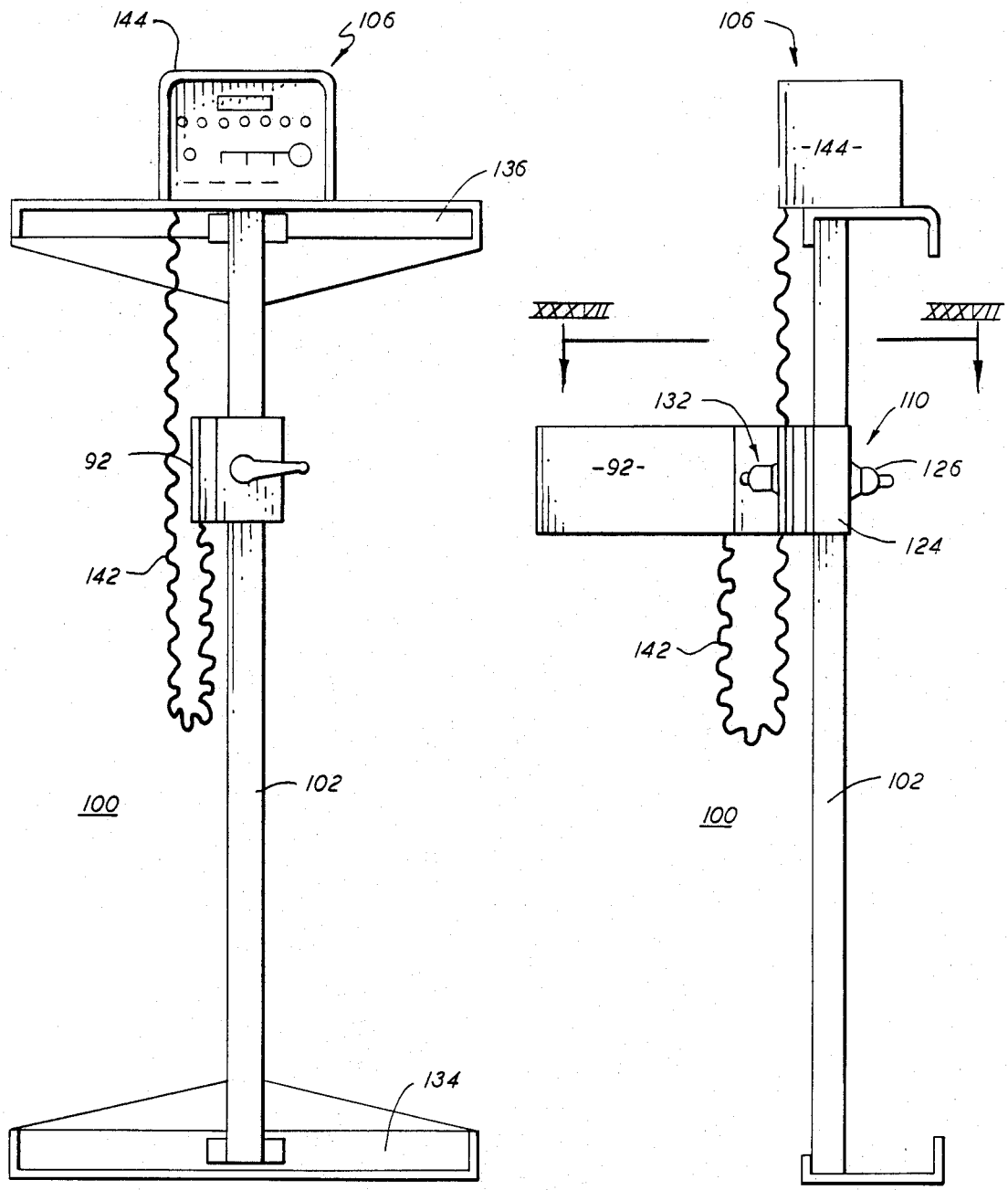
FIGS. 34 and 35 are front and side views, respectively, of a muscle, testing apparatus that may be used in the practice of the present invention.
Figure 36:
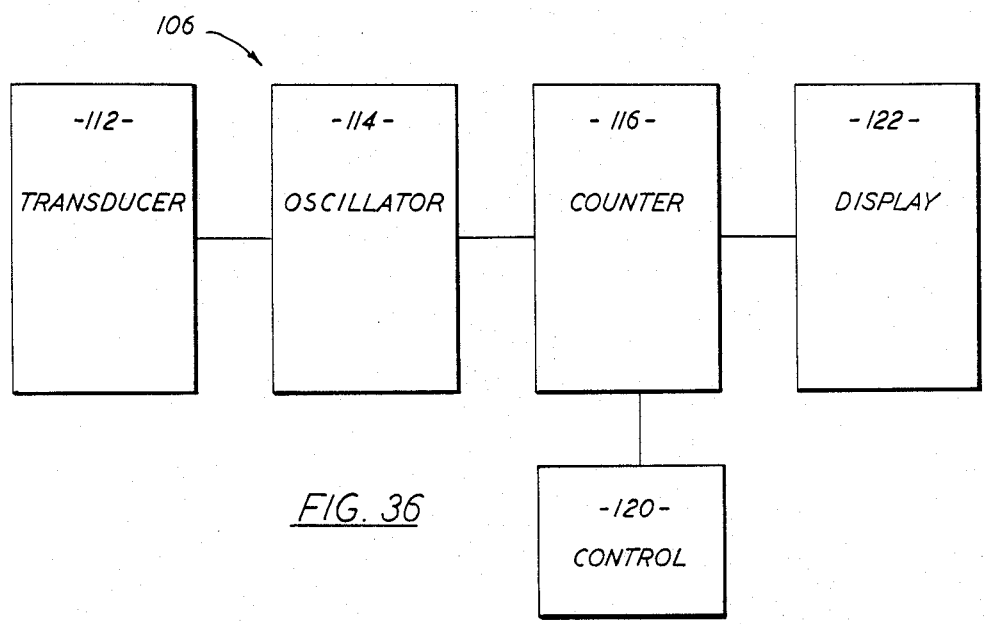
FIG. 36 is a block diagram showing the sensor and display means of the apparatus shown in FIGS. 34 and 35.

FIGS. 34 and 35 illustrate muscle testing apparatus 100 that may be used to carry out the present invention; and generally this apparatus comprising guide means 102, the above-mentioned pressure pad 92, sensing and display means 106, and connecting means 110. Preferably, as shown in FIG. 36, sensing an display means 106 includes pressure transducer 112, capacitance oscillator 114, counter 116, counter control means 120, and display means 122. With reference to FIGS. 34, 35, 37 and 38, connecting means 110 includes slide assembly 124, means 126 connecting that assembly to guide means 102, support arm 130, and means 132 connecting that arm to the slide assembly.

Guide means 102 is provided to guide movement of pressure pad 92 along a predefined path, and for example the guide means may comprise a vertically extending post. In use, guide means 102 itself may be supported in any acceptable way. For instance, first bracket 134 may securely connect a lower end of guide means 102 to a floor or a wall, and second bracket 136 may securely connect an upper end of the guide means to that wall or to a ceiling.

Pressure pad 92 comprises an inflatable flexible bag having a generally flat rectangular shape, forming generally planar front and back faces. A flat strip of hook and pile type fasteners, such as velcro, is connected to the back face of the pressure pad to hold the pad in place in apparatus 100, in a manner discussed in detail below. In use, pad 92 is filled with a gas, such as ambient air, to a preset pressure.

Sensing and display means 106 is connected to pressure pad 92 to sense the force applied to that pad and to generate a signal providing a quantitative measure of that force. In particular, pressure transducer 112 is connected to pressure pad 92 via line 142 (shown in FIGS. 34 and 35) so that the pressure on the transducer is equal to the pressure in the pressure pad, and the transducer generates an electric current proportional to the extent to which the pressure on the transducer exceeds a threshold pressure.

With reference to FIG. 36, variable capacitance oscillator 114 is connected to transducer 112 to receive the current generated thereby, and the oscillator generates an electric current pulse at a variable frequency dependent on the magnitude of the current conducted to the oscillator. In particular, the frequency of this current pulse increases and decreases, although not necessarily linearly, with the magnitude of the current generated by the transducer 112.

Counter 116 is connected to variable capacitance oscillator 114 to count the electric pulse signals generated by the oscillator, and counter control means 120 is connected to counter 116 to count only those pulses from oscillator 114 that are generated during a test period. In this way, the number of pulses counted by counter 116 provides a quantitative and objective indication of the amount of force applied to pressure pad 92 over that test period. Preferably, counter control means 120 is designed so that an operator may select the length of the test period from among a multitude of possible time lengths such as five, ten, twenty, thirty, forty, or sixty seconds.

Display means 122 is connected to counter 116 to display the number of the electric pulse signal generated by variable capacitance oscillator 114 during a test period. Display means 122 receives the output signal from the counter 116 and converts the output signal into one or more electric signal that are used to show a number that is equal to the number of pulse signals generated by oscillator 114. This number may be shown in a variety of different ways; and, for example, display means 122 may comprise a four character display board, with each character comprised of seven LED segments, designed to show the numbers 0 to 9999.

Pressure transducers, variable capacitance oscillators, pulse counters, and display means of the above-described types are all well-known devices. Any suitable devices of these types may be used to practice the present invention, and it is unnecessary to explain the details of these components further herein. Moreover, the various elements of sensing and display means 106 may be located in or connected to a protective housing 144, which in turn may be mounted on top bracket 136.

With reference again to FIGS. 34 and 35, connecting means 110 connects pressure pad 92 to guide means 102, and this connecting means is adjustable between locked and unlocked positions. In the locked position, connecting means 110 securely holds pressure pad 92 in a fixed position relative to guide means 102; and when connecting means 110 is in the unlocked position, pressure pad 92 is slideable along the guide means 102, and pivotally moveable about a horizontal axis. With this mobility and maneuverability, pressure pad 92 may be easily adjusted between and securely held in a multitude of different positions, in which the pressure pad may be readily engaged by many different body areas to test the strengths of a multitude of different muscles and muscle groups. Moreover, for each of these positions of pressure pad 92, the front face thereof may be located at least substantially perpendicular to the direction of the force developed by the muscle or muscle group being tested.

Figure 37:
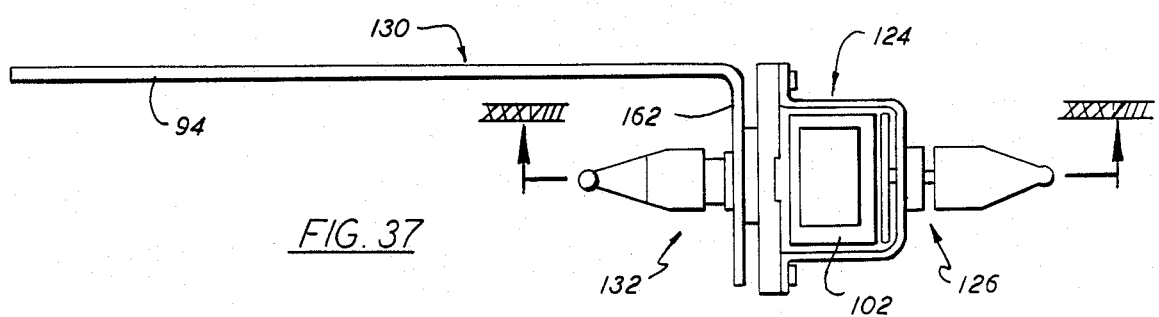
FIG. 37 is a top view of several connected parts of the apparatus shown in FIGS. 34 and 35, taken along line XXXVII—XXXVII of FIG. 35.
Figure 38:
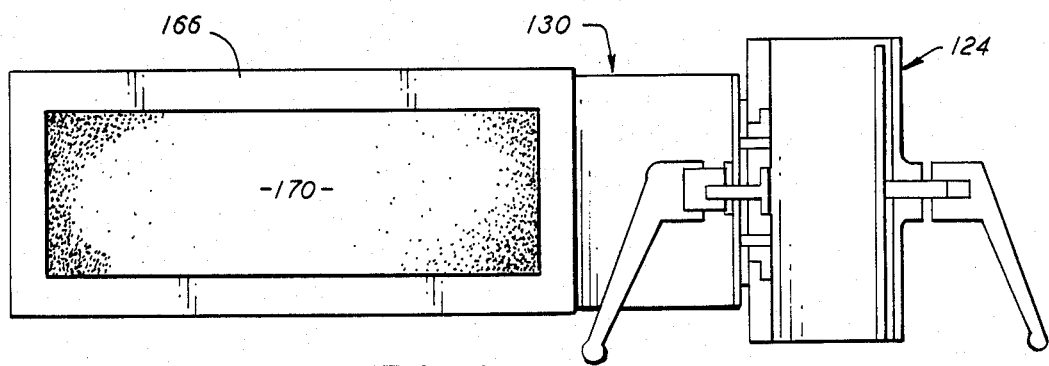
FIG. 38 is a side view, partially in cross section, taken along line XXXVIII—XXXVIII of FIG. 37.

As is believed best shown in FIGS. 37 and 38, slide assembly 124 of connecting means 110 is mounted on guide means 102, and connecting means 126 connects slide assembly 124 to guide means 102. This connecting means 126 has a locked position securely holding slide assembly 124 in a fixed position on guide means 102, and an unlocked position wherein the slide assembly is slideable along the guide means.

Support arm 130 extends away from slide assembly 124, and the support arm 130 includes first leg 162 and a second leg that forms the above-mentioned rigid support plate 94. Legs 162 and 164 are connected together to form an L-shaped bracket; and a sleeve 166 extends around and is tightly fitted on leg 94, and thus forms front and rear faces. Flat, rectangular strips 170 of hook and pile type fasteners are secured to these faces of sleeve 166, and pressure pad 92 may be connected, by means of its own fastener strip, to either of strips 170, and thus may be located on either side of leg 94.

Connecting means 132 connects support arm 130 to slide assembly 124, and this connecting means 132 also has locked and unlocked positions. In its locked position, connecting means 132 securely holds support arm 130 in a fixed position relative to slide assembly 124; and in its unlocked position, connecting means 132 supports arm 130 for pivotal movement about a horizontal axis.

Preferably, apparatus 100 further includes a pump (not shown) to pressurize pressure pad 92. This may be done occasionally, for example at the start of a day, to replace any air that might have escaped from the pressure pad 92 and to bring the pressure inside the pad to a preset or standard level. Any suitable pump may be used to do this, and the pump may also be located inside display housing 144

To prepare apparatus 100 for operation, guide means 102 is secured in place via brackets 134 and 136, and the pressure pad 92 is brought to a desired pressure level. To test a particular muscle or muscle group of a subject, the subject stands or sits next to apparatus 100, and pressure pad 92 is positioned, as explained above in detail, so that it may be engaged by a body area that may be moved by that particular muscle or muscle group, with the front face of the pressure pad face perpendicular to the direction of the force developed by the muscle or muscle group. It is believed that best results are obtained if pad 92 is located at the middle of the arc, or range of motion, through which the body area would normally move as a result of the force applied to the body area by the muscle or muscle group being tested.

Pressure pad 92 is located in this particular position by locking slide assembly 124 at a selected height, and locking support arm 130 at a selected angle relative to the vertical. An operator may wish to record this selected height and angle; and guide means 102, slide assembly 124 and support arm 130 are provided with markings to indicate these measurements. Also, a graph or chart may be located on the floor adjacent apparatus 100 so that the operator can record the subject's position relative to the apparatus.

At the start of a test period, the subject flexes the muscle or muscle group under study to apply a force to pressure pad 92, and the subject continues to apply this force to the pressure pad until the end of the test period. The magnitude of the force applied to pressure pad 92 is sensed by sensing and display means 106, which produces a quantitative signal representing that force, and in particular, a quantitative signal representing the amount of the force applied to pressure pad 104 over the test period, which indicates the endurance of the muscle being tested. The results of the test may then be recorded and compared with the results of other tests to provide a quantitative comparison of changes in a patient's muscle or muscle group. For example, the test results may show that a particular muscle has become stronger as a result of an exercise program.

An important advantage of the present invention, especially when used with the above-described apparatus, is that particular test procedures can be reproduced identically, or at least very substantially so, at different times. The position or location of the subject relative to apparatus 100, and the height and angular orientation of pressure pad 92, can all be recorded with a very high degree of precision; and the relative positions of apparatus 100, pressure pad 92 and the subject can all be reproduced at a later time with a very high degree of accuracy. Moreover, because the test results are objective and quantitative, first, those results are very reliable, and second, the test results are very well suited for comparison with earlier or later test results to yield accurate and valuable information about changes in the strengths of a subject's muscles.

While it is apparent that the invention disclosed herein is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed is:

1. A method of testing the strength of a selected muscle or muscle group of a human subject, comprising the steps of:
    (a) stabilizing the subject's body and determining the range of motion of a body area moved by a selected muscle or muscle group;
    (b) locating a force sensing means in said range by moving the sensing means along a guide means to a selected height, and then pivoting the sensing means about a rotational axis to a selected angular orientation within said range;
    (c) contacting the sensing means with said body area;
    (d) flexing the muscle or muscle group to force the body area against the sensing means;
    (e) isolating the selected muscle or muscle group so that at least substantially all the force applied to the sensing means by the body area is due to the flexing of the selected muscle or muscle group;
    (f) measuring the force applied against the sensing means for a predetermined test period by producing a signal representing the measure force; and
    (g) recording the selected height and angular orientation of the sensing means, the force applied, and the location of the subject relative to the guide means.

2. A method according to claim 1, wherein the selected muscle or muscle group is the sternocleidomastoid muscle, and wherein:
    the locating step includes the step of positioning the sensing means directly forward of a head of the subject;
    the contacting step includes the step of engaging the sensing means with a top part of a face of the subject; and
    the flexing step includes the step of flexing the sternocleidomastoid muscle to apply a forward and downward force on the sensing means.

3. A method according to claim 1, wherein the selected muscle or muscle group comprises a piriformis muscle, and wherein:
    the stabilizing step includes the step of placing the subject in a standing position;
    the locating step includes the step of positioning the sensing means behind and laterally to a side of a leg of the subject, with the sensing means facing forward and inward;
    the contacting step includes the step of engaging the sensing means with a back of the leg, toward a lateral side thereof; and
    the flexing step includes the step of flexing the piriformis muscle to apply a laterally outward and rearward force on the sensing means.

4. A method according to claim 3, wherein
    the step of positioning the sensing means includes the step of positioning the sensing means behind and to a lateral side of a thigh of the leg;
    the engaging step includes the step of engaging the sensing means with the thigh of the leg;
    the contacting step further includes the step of holding the thigh of the leg and a lower part of the leg aligned during the flexing step; and
    the subject is standing on a floor, and the isolating step includes the step of holding a foot of the leg off the floor.

5. A method of testing the strength of a selected muscle or muscle group of a human subject, comprises the steps of:
   (a) stabilizing the subject's body and determining the range of motion of a body area moved by a selected muscle or muscle group,
   (b) locating a force sensing means within the range of movement of the body area by moving the sensing means along a guide means to a selected position, and pivoting the sensing means about a rotational axis to a selected angular orientation,
   (c) contacting the body area with a force sensing means to isolate the selected muscle or muscle group for testing,
   (d) flexing the muscle or muscle group so that substantially all of the force applied to the sensing means by the body area is due to the flexing of the selected muscle or muscle group,
   (e) measuring the force applied against the sensing means for a selected test period,
   (f) recording the force applied, the selected position, the angular orientation of the sensing means and the location of the subject as stabilized.

6. A method according to claim 1 or 5, wherein the locating step includes the step of positioning the force sensing means substantially in the middle of said range.

7. A method according to claim 1 or 5, wherein the selected muscle or muscle group is a sternocleidomastoid muscle, and wherein:
   the locating step includes the step of positioning the sensing means to a left side of a head of the subject;
   the contacting step includes the step of engaging the sensing means with the left side of the head, behind an ear of the subject; and
   the flexing step includes the step of flexing the sternocleidomastoid muscle to apply a laterally outward and downward force on the sensing means.

8. A method according to claim 1 or 5, wherein the selected muscle or muscle group is a sternocleidomastoid muscle, and wherein:
   the locating step includes the step of positioning the sensing means to a right side of a head of the subject;
   the contacting step includes the step of engaging the sensing means with the side of the head, forward of an ear of the subject; and
   the flexing step includes the step of flexing the sternocleidomastoid muscle to apply a sideward and downwards force on sensing means.

9. A method according to claim 1 or 5, wherein the selected muscle or muscle group is an anterior deltoid muscle, and wherein:
   the locating step includes the step of positioning the sensing means directly forward of an arm of the subject;
   the contacting step includes the step of engaging the sensing means with a front of the arm; and
   the flexing step includes the step of flexing the anterior deltoid to apply a forward and upward force on the sensing means.

10. A method according to claim 9, wherein the positioning step includes the step of positioning the sensing means directly forward of an upper part of the arm, with the sensing means facing rearward and downward;
   the engaging step includes the steps of
      (i) positioning the arm with a palm of a hand of the arm directed forward, and
      (ii) engaging the sensing means with a front of the upper part of the arm.

11. A method according to claim 1 or 5, wherein the selected muscle or muscle group is a pectoralis major muscle, and wherein:
   the locating step includes the step of positioning the sensing means forward of and to a lateral side of the subject;
   the contacting step includes the steps of
      (i) extending an arm of the subject laterally outward and upward from a shoulder of the subject, and
      (ii) engaging the sensing means with a front of the arm; and
   the flexing step includes the step of flexing the pectoralis major muscle to apply a forward force on the sensing means.

12. A method according to claim 11, wherein: the sensing means is positioned slightly to the lateral side of the subject and approximately at the level of the shoulder; and
   the engaging step includes the steps of
      (i) holding the arm with a palm of a hand of the arm directed forwardly, and
      (ii) engaging the sensing means with a front part of an upper part of the arm.

13. A method according to claim 1 or 5, wherein the selected muscle or muscle group comprise a rectus abdominus muscle, and wherein:
   the step of stabilizing the patient includes the step of seating the patient in a chair with a back of the patient slanting rearwardly upwardly and resting against a back of the chair;
   the locating step includes the step of positioning the sensing means forward and above a chest of the subject;
   the contacting step includes the step of engaging the sensing means with the chest; and
   the flexing step includes the step of flexing the rectus abdominus muscle to apply an upward and forward force on the sensing means.

14. A method according to claim 13 wherein:
   the step of positioning the sensing means includes the step of facing the sensing means rearwardly downwardly; and
   the isolating step includes the step of keeping thighs of the subject stationary.

15. A method according to claim 1 or 5, wherein the selected muscle or muscle group is a bicep of an arm of the subject, and wherein:
   the locating step includes the step of positioning the sensing means directly forward of the arm:
   the contacting step includes the steps of
      (i) extending a forearm of the arm forward, and
      (ii) engaging the sensing means with a top of the forearm; and
   the flexing step includes the step of flexing the bicep muscle to apply an upward force to the sensing means.

16. A method according to claim 15, wherein:
   the step of positioning the sensing means includes the step of facing the sensing means downward; and
   the extending step includes the step of extending the forearm to a horizontal position, with a palm of a hand of the arm directed upward.

17. A method according to claim 1 or 5, wherein the selected muscle or muscle group comprise finger flexor muscles, and wherein:

the contacting step includes the step of grabbing the sensing means with a thumb and fingers of a hand of the subject; and the flexing step includes the step of flexing the finger flexor muscles to squeeze the sensing means between the thumb and the fingers.

18. A method according to claim 1 or 5, wherein the selected muscle or muscle group comprise sartorius and gracilus muscles, and wherein:

the stabilizing step includes the step of seating the subject;

the locating step includes the steps of positioning the sensing means between lower parts of legs of the subject, and facing the sensing means laterally outwardly and downwardly toward one of the lower parts;

the contacting step includes the step of engaging the sensing means with an inside of the one of the lower parts of the legs; and the flexing step includes the step of flexing the sartorius and gracilus muscles to apply an inward and upward force on the sensing means.

19. A method according to claim 1 or 5, wherein the selected muscle or muscle group comprise a quadricep muscle, and wherein:

the stabilizing step includes the step of seating the patient;

the locating step includes the step of positioning the sensing means directly forward of a lower part of a leg of the subject;

the contacting step includes the step of contacting the sensing means with a front of the lower part of the leg;

the flexing step includes the step of flexing the quadricep muscles to apply a forward and upward force on the sensing means.

20. A method according to claim 19, wherein:

the subject is seated in a chair above a floor;

the isolating step includes the step of keeping a foot of the leg off the floor; and the positioning step includes the step of facing the sensing means rearward and downward.

21. A method according to claim 1 or 5, wherein the selected muscle or muscle group is an anterior tibial muscle, and wherein:

the stabilizing step includes the step of seating the subject;

the locating step includes the step of positioning the sensing means above a foot of a leg of the subject;

the contacting step includes the step of engaging the sensing means with a top of the foot; and the flexing step includes the step of flexing the anterior tibial muscle to apply an upward and rearward force on the sensing means.

22. A method according to claim 21, wherein:

the step of positioning the sensing means includes the step of facing the sensing means downwardly and forwardly;

the subject is seated in a chair, above a floor, and the isolating step includes the step of holding the foot off the floor.

23. A method according to claim 1 or 5, wherein the selected muscle or muscle group comprise peroneus longus and peroneus brevis muscles, and wherein:

the stabilizing step includes the step of seating the subject;

the locating step includes the step of positioning the sensing means between the legs of the subject;

the contacting step includes the step of engaging the sensing means with a bottom of a foot of one of the legs of the subject; and the flexing step includes the step of flexing the peroneus longus and the peroneus brevis muscles to apply an inward and downward force on the sensing means.

24. A method according to claim 23, wherein:

the subject is seated in a chair, above a floor;

the engaging step includes the step of engaging the sensing means with a laterally inward portion of the bottom of the foot; and the isolating step includes the step of keeping the foot of the one of the legs and a foot of a second of the legs off the floor.

25. A method according to claim 1 or 5, wherein the selected muscle or muscle group is a subscapularis muscle, and wherein:

the locating step includes the step of positioning the sensing means laterally inside an arm of the subject;

the contacting step includes the step of engaging the sensing means with an inside of the arm; and the flexing step includes the step of flexing the subscapularis muscle to apply an inward force to the sensing means.

26. A method according to claim 25, wherein:

the engaging step includes the steps of
 (i) extending a forearm of the arm forward to a substantially horizontal position,
 (ii) holding a palm of a hand of the arm directed inward, and
 (iii) engaging the sensing means with an inside surface of the forearm; and the isolating step includes the step of holding an upper part of the arm vertical.

27. A method according to claim 1 or 5, wherein the selected muscle or muscle group is a coracobrachialis muscle, and wherein:

the locating step includes the step of positioning the sensing means forward and to a lateral side of the subject;

the contacting step includes the step of
 (i) extending an arm of the subject forward and laterally outward, and
 (ii) engaging the sensing means with an inside of the arm; and the flexing step includes the step of flexing the coracobrachialis muscle to apply an upward and inward force on the sensing means.

28. A method according to claim 27, wherein:

the step of positioning the sensing means includes the step of facing the sensing means laterally outwardly, downwardly and rearwardly;

the engaging step includes the step of engaging the sensing means with an inside of an upper part of the arm; and the isolating step includes the step of keeping the upper part and a forearm of the arm aligned during the flexing step.

29. A method according to claim 1 or 5, wherein the selected muscle or muscle group is a seratus anterior muscle, and wherein:

the locating step includes the step of positioning the sensing means forward of the subject;

the contacting step includes the steps of
 (i) extending an arm of the subject forward, and
 (ii) engaging the sensing means with a hand of the arm; and the flexing step includes the step of flexing the serratus anterior muscle to apply a forward force on the sensing means.

30. A method according to claim 29, wherein:
the step of positioning the sensing means includes the step of positioning the sensing means at a height level with a shoulder of the subject;
the engaging step includes the step of engaging the sensing means with a palm of the hand; and
the isolating step includes the step of holding a forearm and an upper part of the arm aligned and horizontal during the flexing step.

31. A method according to claim 1 or 5, wherein the selected muscle or muscle group is a quadratus lumborum muscle, and wherein:
the locating step includes the step of positioning the sensing means between a chest and an arm of the subject;
the contacting step includes the step of contacting the sensing means with an outside of the chest; and
the flexing step includes the step of flexing the quadratus lumborum muscle to apply an outward force on the sensing means.

32. A method according to claim 31, wherein:
the step of positioning the sensing means includes the step of facing the sensing means laterally inwardly and upwardly; and
the isolating step includes the step of holding the arm away from the sensing means.

33. A method according to claim 1 or 5, wherein the selected muscle or muscle group comprise psoas and iliacus muscles, and wherein:
the stabilizing step includes the step of seating the patient;
the locating step includes the step of positioning the sensing means forward of the subject, between legs thereof;
the contacting step includes the step of extending one of the legs forward, and engaging the sensing means with an inside of the one of the legs; and
the flexing step includes the step of flexing the psoas and iliacus muscles to apply an inward and upward force to the sensing means.

34. A method according to claim 33, wherein:
the step of positioning the sensing means includes the step of positioning the sensing means at the level of a waist of the subject;
the extending step includes the step of raising a lower part of the one of the legs to a position extending forward and upward from a thigh of the one of the legs, and holding the lower part and the thigh of the one of the legs aligned; and
the engaging step includes the step of engaging the sensing means with an inside of the lower part of the one of the legs.

35. A method according to claim 34, wherein:
the subject is seated in a chair, above a floor; and
the isolating step includes the steps of
(i) raising the thigh of the one of the legs off the chair, and
(ii) holding a foot of another one of the legs off the floor.

36. A method according to claim 1 or 5, wherein the selected muscle or muscle group comprise an adductor longus muscle and an adductor magnus muscle, and wherein:
the locating step includes the step of positioning the sensing means between legs of the subject, with the sensing means facing laterally outward toward one of the legs;
the contacting step includes the step of engaging the sensing means with an inside of the one of the legs;
the flexing step includes the step of flexing the adductor longus and the adductor magnus muscles to apply a downward and laterally inward force on the sensing means.

37. A method according to claim 36, wherein:
the stabilizing step includes the step of placing the subject in a standing position;
the step of positioning the sensing means includes the step of positioning the sensing means between lower parts of the legs, facing laterally outward and upward; and
the engaging step includes the step of engaging the sensing means with an inside of the lower part of the one of the legs; and
the isolating step includes the step of holding the lower part and a thigh of the one of the legs aligned during the flexing step.

38. A method according to claim 1 or 5, wherein the selected muscle or muscle group comprises a splenius capitus and cervicis muscle, and wherein:
the locating step includes the step of positioning the sensing means behind a neck of the subject;
the contacting step includes the step of engaging the sensing means with a back of a head of the subject; and
the flexing step includes the step of flexing the splenius capitus and cervicis muscle to apply a downward and rearward force on the sensing means.

39. A method according to claim 38, wherein:
the positioning step includes the step of facing the sensing means upward and forward; and
the engaging step includes the step of engaging the sensing means with the back of the head, approximately midway along the height of the back of the head.

40. A method according to claim 1 or 5, wherein the selected muscle or muscle group comprises an upper trapezius muscle, and wherein:
the locating step includes the step of positioning the sensing means on a shoulder of the subject, and holding the sensing means between the shoulder and a side of a head of the subject; and
the flexing step includes the step of flexing the upper trapezius muscle to squeeze the sensing means between the shoulder and the side of the head.

41. A method according to claim 40, wherein:
the holding step includes the step of raising the shoulder and pivoting an arm of the subject laterally outward to help hold the sensing means on the shoulder; and
the engaging step includes the step of engaging the sensing means with the side of the head, behind an ear of the subject.

42. A method according to claim 1 or 5, wherein the selected muscle or muscle group comprises major and minor rhomboid muscles and a trapezius muscle, and wherein:
the locating step includes the step of positioning the sensing means laterally to a side of the subject;
the contacting step includes the steps of
(i) extending an arm of the subject laterally outwardly, and
(ii) engaging the sensing means with a back of the arm; and the flexing step includes the step of flexing the major and minor rhomboid muscles and the trapezius muscle to apply a rearward force on the sensing means.

43. A method according to claim 42, wherein:
the extending step includes the steps of
(i) raising the arm to a horizontal position,
(ii) holding a forearm and an upper part of the arm aligned during the flexing step, and
(iii) holding the arm with a palm of a hand of the arm directed downward; and
the engaging step includes the step of engaging the sensing means with a back of an upper part of the arm.

44. A method according to claim 1 or 5, wherein the selected muscle or muscle group comprises a deltoid muscle, and wherein:
the locating step includes the step of positioning the sensing means laterally to a side of the subject;
the contacting step includes the step of engaging the sensing means with an outside of an arm of the subject; and
the flexing step includes the step of flexing the deltoid muscle to apply an upward and outward force on the sensing means.

45. A method according to claim 44, wherein:
the step of positioning the sensing means includes the step of positioning the sensing means facing downwardly and inwardly, at a level slightly below a top of a shoulder of the subject; and
the engaging step includes the steps of
(i) engaging the sensing means with an outside of an upper part of the arm, and
(ii) holding a forearm of the arm at approximately a right angle to the upper part of the arm.

46. A method according to claim 1 or 5, wherein the selected muscle or muscle group comprises a latissimus dorsi muscle and a teres major muscle and wherein:
the locating step includes the step of positioning the sensing means facing upward and to a lateral side of the subject;
the contacting step includes the steps of:
(i) raising an arm of the subject above the sensing means, and
(ii) engaging the sensing means with a bottom of the arm; and
the flexing step includes the step of flexing the latissimus dorsi and the teres major muscles to apply a downward and inward force on the sensing means.

47. A method according to claim 46, wherein:
the raising step includes the steps of
(i) extending the arm forwardly laterally,
(ii) holding an upper part of the arm horizontal, and
(iii) holding a forearm of the arm vertical; and
the engaging step includes the step of engaging the sensing means with a bottom of the upper part of the arm.

48. A method according to claim 1 or 5, wherein the selected muscle or muscle group comprises a tricep muscle, and wherein:
the locating step includes the step of positioning the sensing means directly forward of an arm of the subject;
the contacting step includes the step of
(i) raising a forearm of the arm to a horizontal position, and
(ii) engaging the sensing means with a bottom of the forearm; and
the flexing step includes the step of flexing the tricep to apply a downward force on the sensing means.

49. A method according to claim 48, wherein the raising step includes the step of holding an upper part of the arm vertical, and extending the forearm directly forward of the upper part of the arm.

50. A method according to claim 1 or 5, wherein the selected muscle or muscle group comprises a gluteous medius muscle, and wherein:
the locating step includes the step of positioning the sensing means to a lateral side of a leg of the subject;
the contacting step includes the step of contacting the sensing means with an outside of the leg; and
the flexing step includes the step of flexing the gluteous medius muscle to apply an outward and upward force on the sensing means.

51. A method according to claim 50, wherein:
the stabilizing step includes the step of placing the patient in a standing position;
the step of positioning the sensing means includes the step of positioning the sensing means directly to a side of a lower part of the leg, with the sensing means slanting facing downwardly and laterally inwardly; and
the contacting step includes the steps of:
(i) contacting the sensing means with an outside of the lower part of the leg, and
(ii) holding the lower part of the leg and a thigh of the leg aligned during the flexing step.

52. A method according to claim 1 or 5, wherein the selected muscle or muscle group comprises a gluteous maximus muscle, and wherein:
the stabilizing step includes the step of placing the subject in a standing position;
the locating step includes the step of positioning the sensing means rearward of a leg of the subject, with the sensing means facing forward;
the contacting step includes the step of engaging the sensing means with a back of a thigh of the leg; and
the flexing step includes the step of flexing the gluteous maximus muscle to apply a rearward and upward force on the sensing means.

53. A method according to claim 52, wherein:
the step of positioning the sensing means includes the step of facing the sensing means forwardly downwardly; and
the isolating step includes the step of holding a lower part of the leg generally horizontal during the flexing step.

54. A method according to claim 1 or 5, wherein the selected muscle or muscle group comprise bicep femorus, semitendinosus and simimembranosus muscles, and wherein:
the stabilizing step includes the step of seating the patient;
the locating step includes the step of positioning the sensing means directly behind a lower part of a leg of the subject;
the contacting step includes the step of engaging the sensing means with a back of the lower part of the leg; and
the flexing step includes the step of flexing the semitendinosus and semimembranosus muscles to apply a downward and rearward force on the sensing means.

55. A method according to claim 54, wherein:

the contacting step further includes the step of bending the leg at a knee thereof; and the subject is seated in a chair, above a floor, and the isolating step includes the step of holding a foot of the leg of the subject off the floor.

56. A method according to claim 1 or 5, wherein the selected muscle or muscle group comprises a gastrocnemius muscle, and wherein:

the stabilizing step includes the step of seating the subject;

the locating step includes the step of positioning the sensing means directly forward of a foot of the subject;

the contacting step includes the step of engaging the sensing means with a bottom of the foot; and the flexing step includes the step of flexing the gastrocnemius muscle to apply a downward and forward force on the sensing means.

57. A method according to claim 56, wherein the subject is seated in a chair, above a floor, and the isolating step includes the step of holding the foot off the floor.

58. A method according to claim 1 or 5, wherein the selected muscle or muscle group comprise a supraspinatus muscle, and wherein:

the locating step includes the step of positioning the sensing means laterally to a side of the subject;

the contacting step includes the steps of extending an arm of the subject laterally outward and downward from a shoulder of the subject, and engaging the sensing means with a back of the arm; and the flexing step includes the step of flexing the supraspinatus muscle to apply a rearward and upward force on the sensing means.

59. A method according to claim 58, wherein:

the step of positioning the sensing means includes the step of positioning the sensing means at a height slightly below the level of the shoulder;

the extending step includes the step of holding an upper part of the arm at an angle of about 30° to the horizontal;

the engaging step includes the step of engaging the sensing means with a back of the upper arm; and the isolating step includes the step of holding forearm of the arm and the upper part of the arm aligned during the flexing step.

60. A method according to claim 1 or 5, wherein the selected muscle or muscle group comprises a teres minor muscle, and wherein:

the locating step includes the step of positioning the sensing means forward of and laterally to a side of the subject;

the contacting step includes the steps of extending a forearm of an arm of the subject forward, and engaging the sensing means with an outside of the forearm; and the flexing step includes the step of flexing the teres minor muscle to apply an outward force on the sensing means.

61. A method according to claim 60, wherein the extending step includes the steps of extending the forearm to a horizontal position, and holding an upper part of the arm vertical.

62. A method according to claim 1 or 5, wherein the selected muscle or muscle group comprises a sacrospinalis muscle, and wherein:

the stabilizing step includes the step of placing the subject in a standing position;

the locating step includes the step of positioning the sensing means directly behind a leg of the subject;

the contacting step includes the step of engaging the sensing means with a back of the leg; and the flexing step includes the step of flexing the sacrospinalis muscle to apply a rearward force on the sensing means.

63. A method according to claim 62, wherein:

the step of positioning the sensing means includes the step of positioning the sensing means directly rearward of a thigh of the leg;

the engaging step includes the steps of
  (i) engaging the sensing means with a back of the thigh, and
  (ii) holding the thigh of the leg and a lower part of the leg aligned during the flexing step; and the subject is standing on a floor, and the isolating step includes the step of holding a foot of the leg off the floor.

64. A method of testing the strength of the sacrospinalis muscle of a human subject, comprising the steps of:

(a) stabilizing the subject by placing the subject in a standing position, and determining the range of motion of a body area moved by the sacrospinalis muscle, (b) locating a force sensing means, by positioning the sensing means directly behind a leg of the subject;

(c) contacting the force sensing means with the body area by engaging the sensing means with a back of the leg, (d) flexing the sacrospinalis muscle to apply a rearward force on the sensing means, (e) isolating the movement of the body area so that substantially all the force applied to the sensing means by the body area is due to the flexing of the sacrospinalis muscle, (f) measuring the force applied against the sensing means for a selected test period and producing a signal representative of the measured force.

* * * * *